US012806033B2

(12) United States Patent
Weiman et al.

(10) Patent No.: US 12,806,033 B2
(45) Date of Patent: Nov. 24, 2026

(54) STABILIZING VERTEBRAE WITH ARTICULATING IMPLANTS

(71) Applicant: GLOBUS MEDICAL, INC., Audubon, PA (US)

(72) Inventors: Mark Weiman, Downingtown, PA (US); Chad Glerum, Pennsburg, PA (US); Ty Hessler, Phoenixville, PA (US); Albert Hill, Richboro, PA (US)

(73) Assignee: Globus Medical, Inc., Audubon, PA (US)

( * ) Notice: Subject to any disclaimer, the term of this patent is extended or adjusted under 35 U.S.C. 154(b) by 0 days.

(21) Appl. No.: 19/086,239

(22) Filed: Mar. 21, 2025

(65) Prior Publication Data

US 2025/0213369 A1 Jul. 3, 2025

Related U.S. Application Data

(63) Continuation of application No. 17/709,973, filed on Mar. 31, 2022, now Pat. No. 12,263,092, which is a continuation of application No. 16/722,214, filed on Dec. 20, 2019, now Pat. No. 11,337,824.

(51) Int. Cl.

*A61F 2/44* (2006.01)
*A61F 2/46* (2006.01)
*A61F 2/30* (2006.01)

(52) U.S. Cl.

CPC .... *A61F 2/4425* (2013.01); *A61F 2002/3008* (2013.01); *A61F 2002/30092* (2013.01); *A61F 2002/30131* (2013.01); *A61F 2002/30624* (2013.01); *A61F 2002/307* (2013.01); *A61F 2002/443* (2013.01); *A61F 2/4455* (2013.01); *A61F 2002/4632* (2013.01); *A61F 2002/4635* (2013.01); *A61F 2310/00329* (2013.01)

(58) Field of Classification Search

CPC .................. A61F 2/4425; A61F 2/4455; A61F 2002/3008; A61F 2002/30092; A61F 2002/30131; A61F 2002/30624; A61F 2002/307; A61F 2002/443; A61F 2002/4632; A61F 2002/4635; A61F 2310/00329

See application file for complete search history.

(56) References Cited

U.S. PATENT DOCUMENTS

2011/0282459 A1 * 11/2011 McClellan, III ...... A61F 2/4425 606/279
2014/0094916 A1 * 4/2014 Glerum ................ A61F 2/4425 623/17.15

* cited by examiner

*Primary Examiner* — Nicholas J Plionis

(57) ABSTRACT

A bone joint spacer has two endplates which have a bone engaging surface on one side, and ramps extending from an opposite side. A shaft has a threaded end, and another end which has ramp followers which mate with the endplate ramps of both endplates. A collar slides over the threaded end of the shaft, and also has ramp followers which mate with the endplate ramps of both endplates. A nut threads onto the end of the shaft and pushes the collar towards the ramp followers of the shaft. This movement causes the ramp followers to slide the ramp followers of the collar and the shaft against the endplate ramps, pushing the endplates apart. Two of these spacers can be combined by a link plate so that the spacers can be aligned or curved into a U-shape to be inserted into the body and positioned between bony surfaces, respectively.

11 Claims, 4 Drawing Sheets

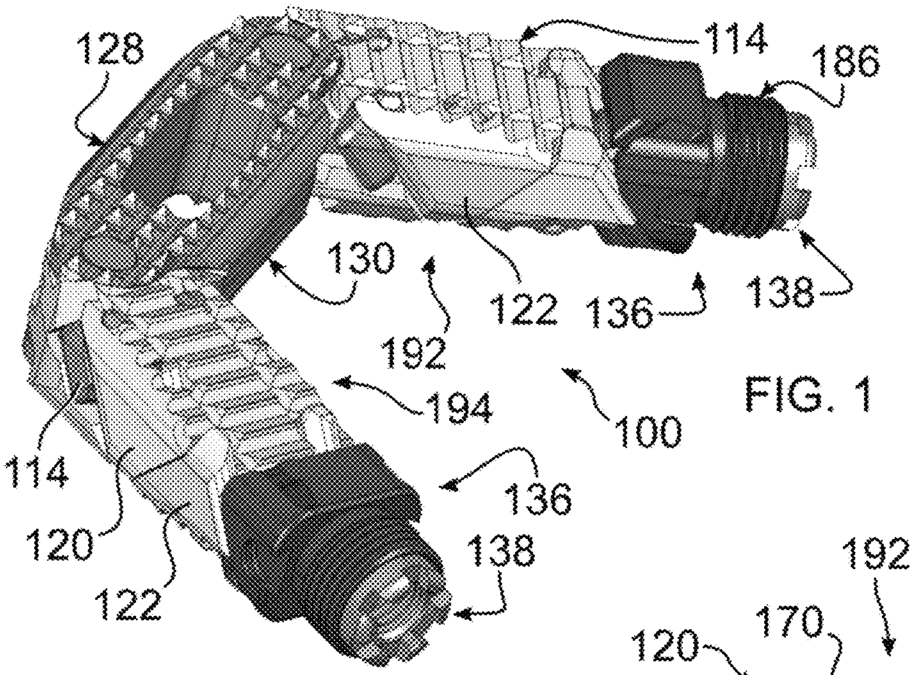
FIG. 1
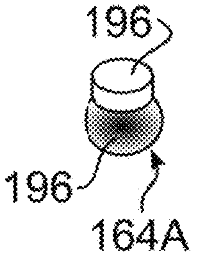
FIG. 2A
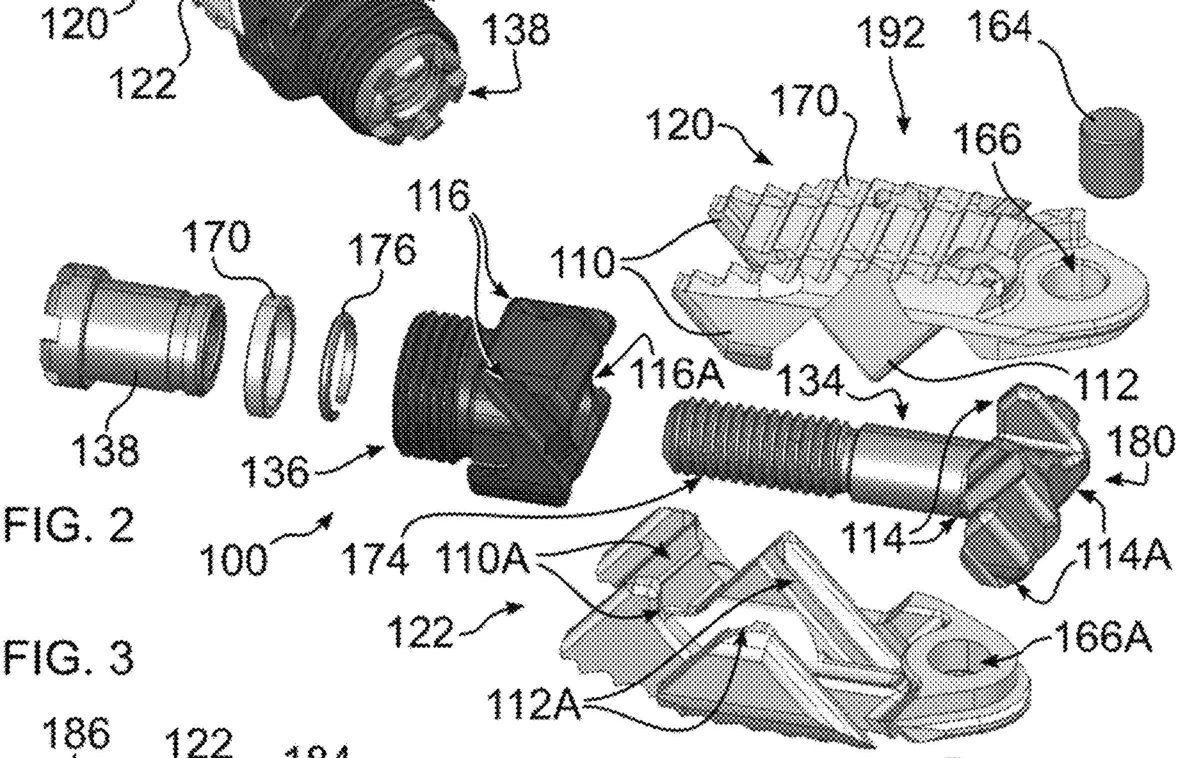
FIG. 2
FIG. 3
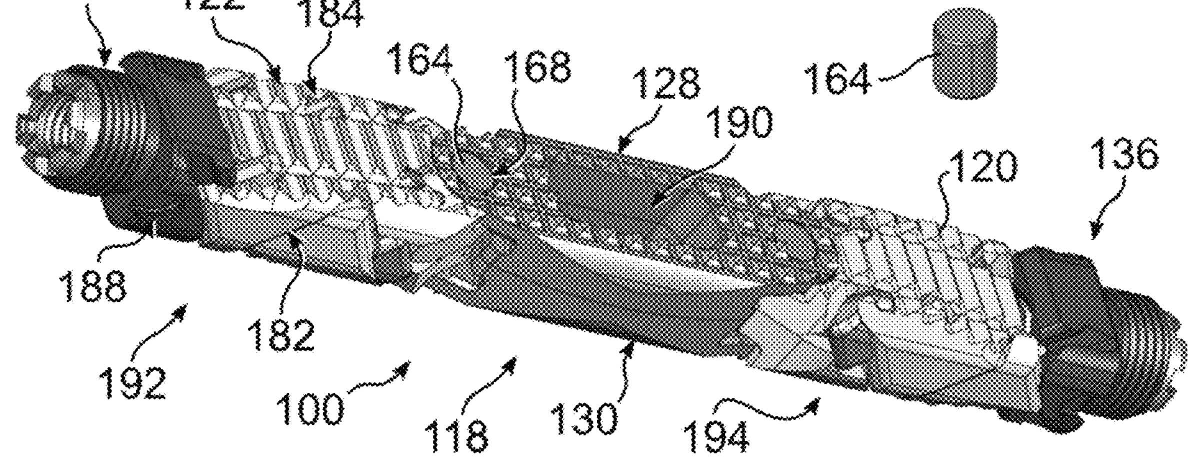

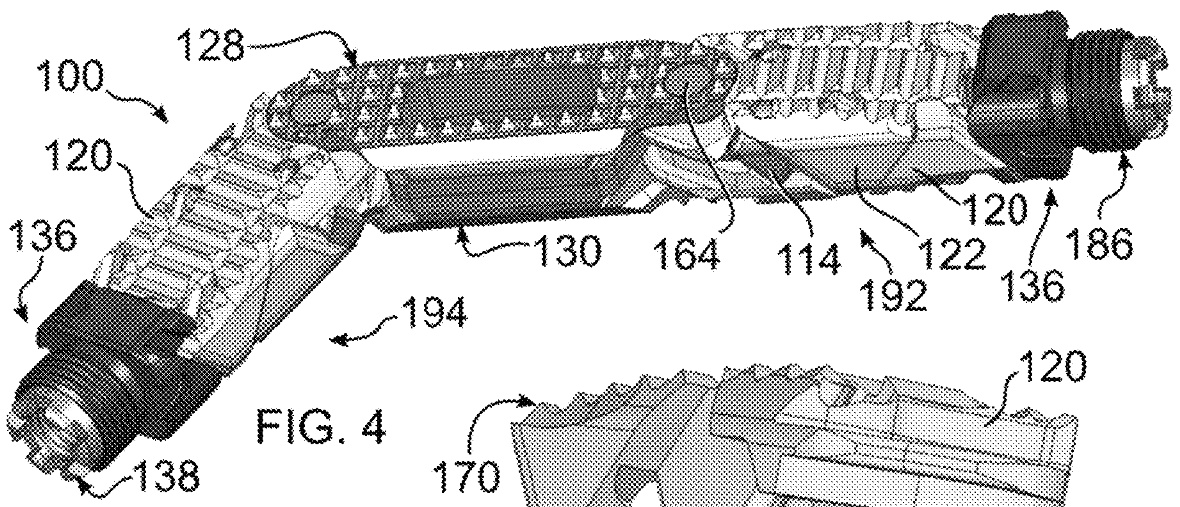
FIG. 4
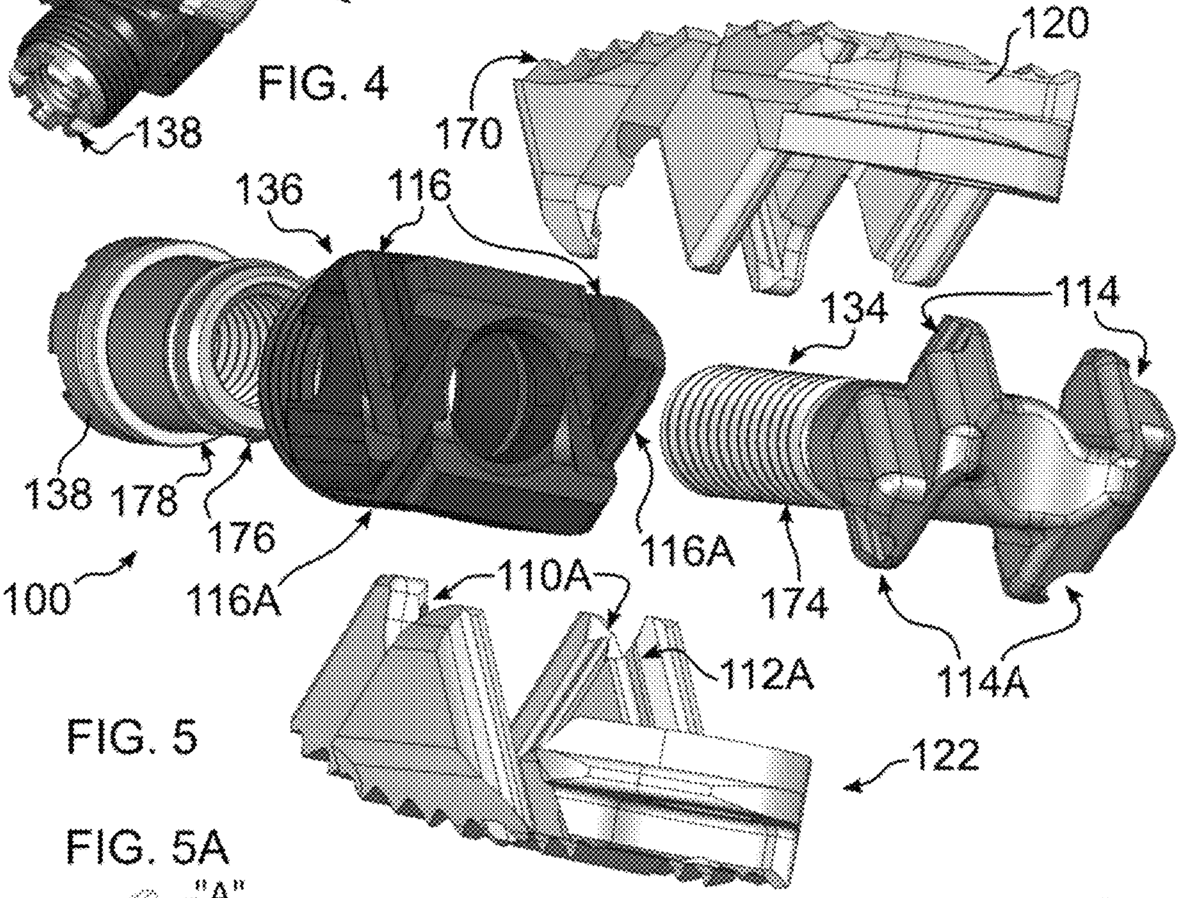
FIG. 5
FIG. 5A
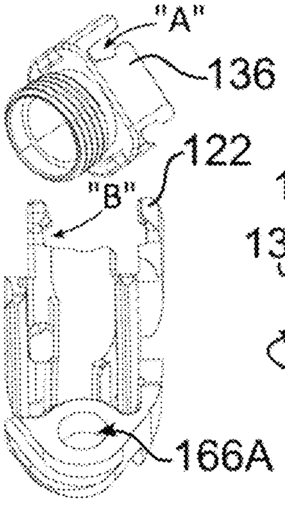
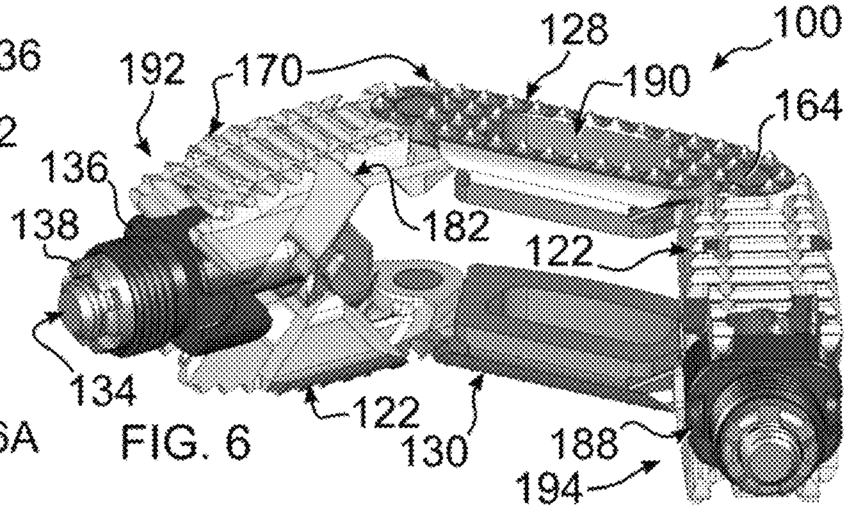
FIG. 6

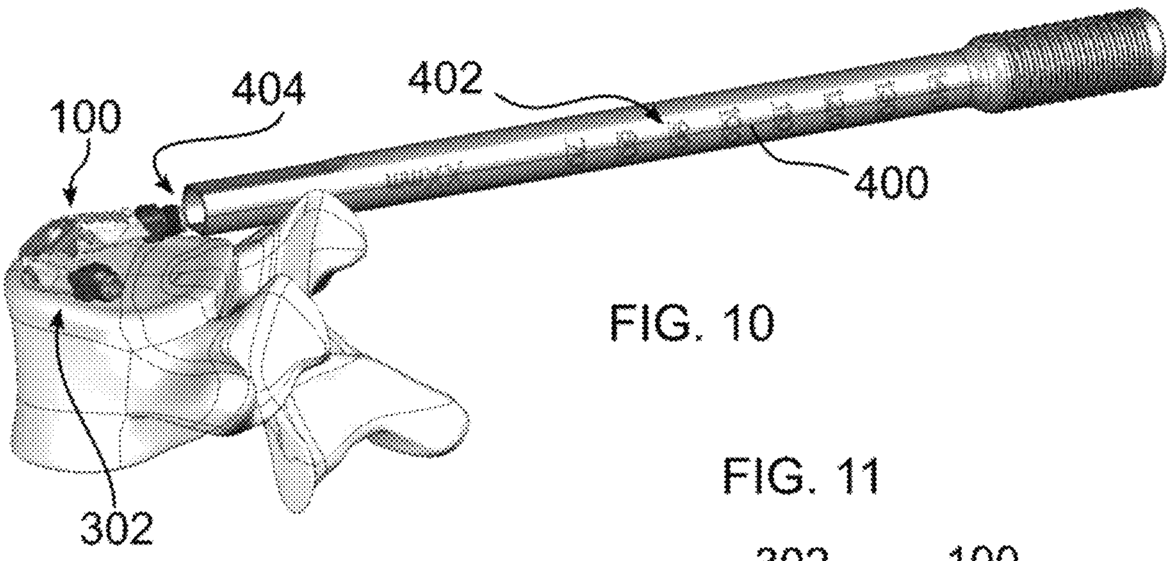
FIG. 10
FIG. 11
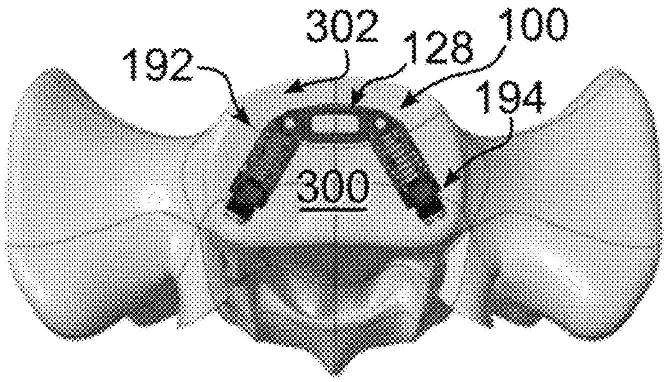

STABILIZING VERTEBRAE WITH ARTICULATING IMPLANTS

CROSS-REFERENCE TO RELATED APPLICATION

This application is a continuation of U.S. patent application Ser. No. 17/709,973 which is a continuation application of U.S. application Ser. No. 16/722,214, filed on Dec. 20, 2019 (published as U.S. Pat. Pub. No. 2021-0186709), which is incorporated by reference herein in its entirety for all purposes.

FIELD OF THE DISCLOSURE

The disclosure relates to a system and method for stabilizing adjacent vertebrae by implanting an articulating interbody implant, and in particular, an implant which articulates to form straight and U-shaped profiles.

BACKGROUND OF THE DISCLOSURE

A common procedure for handling pain associated with intervertebral discs that have become degenerated due to various factors such as trauma or aging is the use of intervertebral fusion devices for fusing one or more adjacent vertebral bodies. Generally, to fuse the adjacent vertebral bodies, the intervertebral disc may first be partially or fully removed. Typically, an intervertebral fusion device may then be inserted between neighboring vertebrae to maintain normal disc spacing and restore spinal stability, thereby facilitating an intervertebral fusion.

There are a number of known conventional fusion devices and methodologies in the art for accomplishing the intervertebral fusion. These include screw and rod arrangements, solid bone implants, and fusion devices which include a cage or other implant mechanism which, typically, is packed with bone and/or bone growth inducing substances. These devices are implanted between adjacent vertebral bodies in order to fuse the vertebral bodies together, alleviating the associated pain.

However, there are drawbacks associated with known conventional fusion devices and methodologies. For example, two important factors in intervertebral fusion may be the anterior (lordotic) angle adjustment and posterior height adjustment. The lordotic angle may be important in restoring sagittal balance while the posterior height may aid in restoring disc height and indirect decompression of the neural foramen. While convention fusion devices may allow for in-situ expansion, they do not allow for the lordotic angle and posterior height to be adjusted in-situ independently of one another, or do not provide adequate solutions to these problems.

SUMMARY OF THE DISCLOSURE

In an embodiment of the disclosure, a spacer for separating bones of a joint comprises first and second endplates, each having a first side forming a bone engaging surface, and a second side opposite to the first side and having at least two ramps extending from the second side in a direction away from the first side; a shaft having a first end having threads, and a second end opposite to the first end having at least two ramp followers each mateable with a ramp of the second side of one of the first and second endplates; a collar slidably disposed upon the shaft proximate the shaft first end, the collar having at least two ramp followers each mateable with a ramp of the second side of one of the first and second endplates; and a nut threadably engaged with the shaft first end, the nut rotatable to push the collar in the direction of the shaft second end to thereby slide the at least two ramp followers of the second end of the shaft and the at least two ramp followers of the collar against mated ramps of the first and second endplates to thereby push the endplates apart relative to each other.

In variations thereof, the nut has a tool engagement surface; the nut and the collar are connected by a split ring; the collar includes an external threaded sleeve engageable by a surgical tool to couple the spacer and the tool; and/or each endplate includes an opening into which a portion of a ramp of another endplate can pass to reduce a height of the spacer.

In further variations thereof, the at least two ramp followers of the second end of the shaft each including a dovetail portion mateable with a ramp of an endplate second side; the at least two ramp followers of the collar each including a dovetail portion mateable with a ramp of an endplate second side; the at least two ramps of the second side include two pairs of ramps; and/or the bone engaging surface includes projections.

In another embodiment of the disclosure, a spacer for separating bones of a joint comprises first and second driven modules, each including: first and second endplates, each having a first side forming a bone engaging surface, and a second side opposite to the first side and having at least two ramps extending from the second side in a direction away from the first side; a shaft having a first end having threads, and a second end opposite to the first end having at least two ramp followers each mateable with a ramp of the second side of one of the first and second endplates; a collar slidably disposed upon the shaft proximate the shaft first end, the collar having at least two ramp followers each mateable with a ramp of the second side of one of the first and second endplates; a nut threadably engaged with the shaft first end, the nut rotatable to push the collar in the direction of the shaft second end to thereby slide the at least two ramp followers of the second end of the shaft and the at least two ramp followers of the collar against mated ramps of the first and second endplates to thereby push the endplates apart relative to each other; and at least one link plate joined to each of the first and second driven modules by a hinge connection.

In a variation thereof, this spacer is used in a method of separating bones of a joint, comprising inserting this joined spacer of claim 10 through an opening in Kambin's triangle and positioning the spacer into a deployment position between vertebral endplates of adjacent vertebrae, the spacer inserted through Kambin's triangle when the endplates are not pushed apart, the endplates driven relatively apart by rotating the nut when the spacer is in the deployment position.

In still further variations thereof, the link plate has first and second spaced apart opposed ends, a hinge including a pin connecting a driven module at each of the first and second ends; the at least one link plate including two link plates, one of the link plates hingedly connected to two first endplates, the other of the two link plates hingedly connected to two second endplates, the two link plates separated from each other when the first and second endplates are pushed apart; and/or the first and second modules and the at least one link plate alignable relative to each other to form a linear spacer, the linear spacer thereby being insertable through a cannula into the body.

In additional variations, the first and second modules are each pivotable about the hinge connection to form the spacer into a U-shaped configuration, the U-shaped configuration formable when the spacer is between two bony surfaces; the hinge connection includes a pin affixed to one of an endplate and link plate, the pin movably connected to the other of the endplate and link plate; the pin forms a curved surface where the pin is movably connected; the collar of each of the two driven modules including an external threaded sleeve engageable by a surgical tool to couple the spacer and the tool; and/or the at least two ramp followers of the collar each including a dovetail portion mateable with a ramp of an endplate second side.

In another embodiment of the disclosure, a spacer for separating bones of a joint comprises: first and second driven modules, each including: first and second endplates, each having a first side forming a bone engaging surface, and a second side opposite to the first side and having at least two spaced apart pairs of ramps extending from the second side in a direction away from the first side; a shaft having a first end having threads, and a second end opposite to the first end having at least two spaced apart pairs of ramp followers each mateable with a pair of ramps of the second side of one of the first and second endplates; a collar slidably disposed upon the shaft proximate the shaft first end, the collar having at least two pairs of ramp followers each mateable with a pair of ramps of the second side of one of the first and second endplates; whereby the pairs of ramps of the first and second endplates face each other, and the bone engaging surfaces of the first and second endplates face in opposite directions relative to each other, when the pairs of ramps of the first and second endplates are mated with the ramp followers of the shaft second end and the collar; and a nut threadably engaged with the shaft first end, the nut rotatable to push the collar in the direction of the shaft second end to thereby slide the at least two pairs of ramp followers of the second end of the shaft and the at least two pairs of ramp followers of the collar against mated ramp pairs of the first and second endplates to thereby push the endplates apart relative to each other; and at least one link plate joined to each of the first and second driven modules by a hinge connection.

BRIEF DESCRIPTION OF THE DRAWINGS

A more complete understanding of the present disclosure, and the attendant advantages and features thereof, will be more readily understood by reference to the following detailed description when considered in conjunction with the accompanying drawings wherein:

FIG. 1 depicts a perspective view of a spacer device of the disclosure, configured in a U-shape as positioned between bones in a patient;

FIG. 2 is an exploded view of one of the two driven modules of FIG. 1;

FIG. 2A is a perspective view of an alternative pin of the device of FIG. 1;

FIG. 3 is a perspective view of the device of FIG. 1, configured in a linear arrangement, as inserted into the body;

FIG. 4 is a perspective view of the device of FIG. 1, with only one of the two driven modules hinged at an angle with respect to link plates joining the driven modules;

FIG. 5 is an alternative exploded view of the device of FIG. 1;

FIG. 5A depicts a collar and endplate of the device of FIG. 1, oriented to show dovetail connections;

FIG. 6 is a perspective view of the device of FIG. 1, expanded into a configuration which separates bones within the body;

FIG. 10 is a perspective diagrammatic view of the device of FIG. 1 during implantation within the body; and FIG. 11 is a top diagrammatic view of an implanted device of FIG. 1.

DETAILED DESCRIPTION OF THE DISCLOSURE

Figure 7:
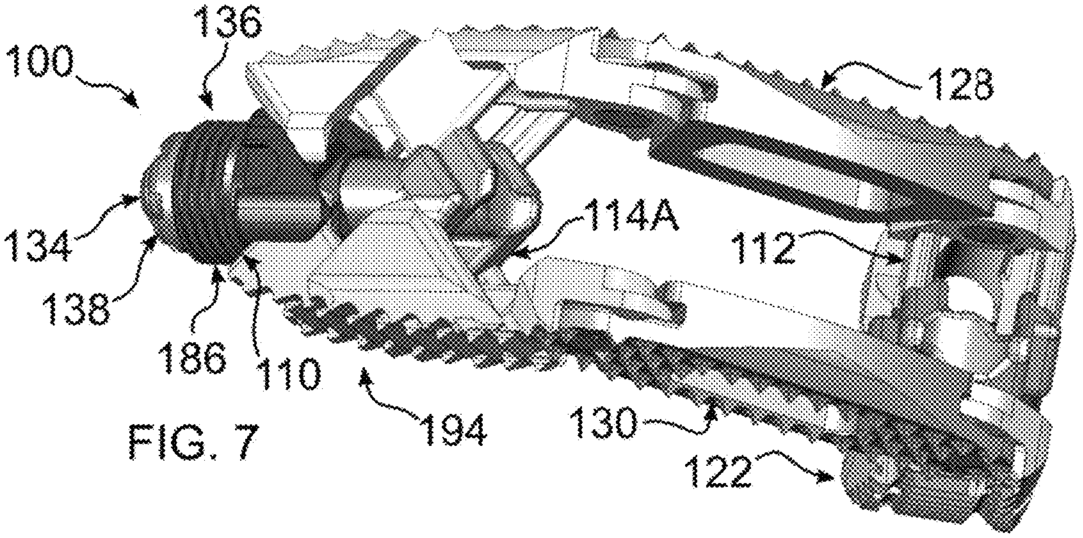
FIG. 7 is an alternative perspective of the device of FIG. 6.

As required, detailed embodiments are disclosed herein; however, it is to be understood that the disclosed embodiments are merely examples and that the systems and methods described below can be embodied in various forms. Therefore, specific structural and functional details disclosed herein are not to be interpreted as limiting, but merely as a basis for the claims and as a representative basis for teaching one skilled in the art to variously employ the present subject matter in virtually any appropriately detailed structure and function. Further, the terms and phrases used herein are not intended to be limiting, but rather, to provide an understandable description of the concepts.

The terms "a" or "an", as used herein, are defined as one or more than one. The term plurality, as used herein, is defined as two or more than two. The term another, as used herein, is defined as at least a second or more. The terms "including" and "having," as used herein, are defined as comprising (i.e., open language). The term "coupled," as used herein, is defined as "connected," although not necessarily directly, and not necessarily mechanically. Headings are provided for the convenience of the reader and are not to be construed as limiting.

With reference to the figures, the disclosure provides an expandable spacer/implant or device 100 having an adjustable height. Device 100 is inserted between two adjacent bony surfaces to facilitate separation of the bones, and if desired, to promote the fusion of bony surfaces. Although intended to be useful with any adjacent bony surface in which fusion is desired, device 100 is advantageously applied to insertion between two adjacent vertebral bodies in any section of the spine, including the cervical, thoracic, lumbar, and sacral vertebral sections. More than one device 100 may be implanted within the body, for example between successive or separated vertebrae, or positioned between the same adjacent vertebrae. The use of multiple devices 100 is particularly advantageous for patients whose back pain is not limited to a localized area, or for patients whose localized damage has progressed to other areas of the spine.

Device 100 and methods for its insertion can be used in a treatment protocol for any of a wide variety of conditions in a patient involving diseased or damaged bony structures. The patient can be a human being. Additionally, it is contemplated that device 100 may be useful in veterinary science for any animal having adjacent bony structures to be fused. Devices 100 can expand to roughly twice its fully reduced insertion height. When in this collapsed configuration, device 100 can be inserted into a space through a small incision and narrow pathways, using appropriate minimally-invasive techniques, and can be positioned within the space between adjacent bones, and there expanded to a desired therapeutic height. The incision may be short, for example about one centimeter in length, which is smaller than device 100 in an expanded configuration. If the desired position and/or expansion are not achieved, device 100 can be collapsed, repositioned, and re-expanded in situ.

Although device 100 is exemplified herein for use in the spine, device 100 is contemplated for fusion of any bony structures. While devices 100 are described herein using several varying embodiments, devices 100 are not limited to these embodiments. An element of one embodiment may be used in another embodiment, or an embodiment may not include all described elements.

Interbody devices have been used to provide support and stability in the anterior column of the spinal vertebrae when treating a variety of spinal conditions, including degenerative disc disease and spinal stenosis with spondylolisthesis. Clinical treatment of spinal pathologies with anterior vertebral body interbody devices relies on precise placement of interbodies to restore normal anterior column alignment. Iatrogenic pathologies may result from both the surgical access window to the disc space, failure to precisely place the interbody on hard cortical bone often found on the apophyseal ring of the vertebral body, or failure to precisely control and restore normal anatomical spinal alignment. Device 100 provides for the precise placement of interbody support that both increases interbody contact with hard cortical bone and provides precise control of anterior column alignment while reducing the profile of the access window to the disc space.

More particularly, in order to improve the access profile of the interbody while maximizing cortical bone contact surface area, device 100 enters the disc space with a narrow profile and articulates to increase surface area contact on the anterior apophyseal ring. The orientation and position of the interbody in its final implanted position may be optimized by pre-/intra-op scans or normal population statistics that determine bone mineral density maps of the vertebral body. Robotic and navigation guidance may be used to correctly orient the interbody.

Figure 8:
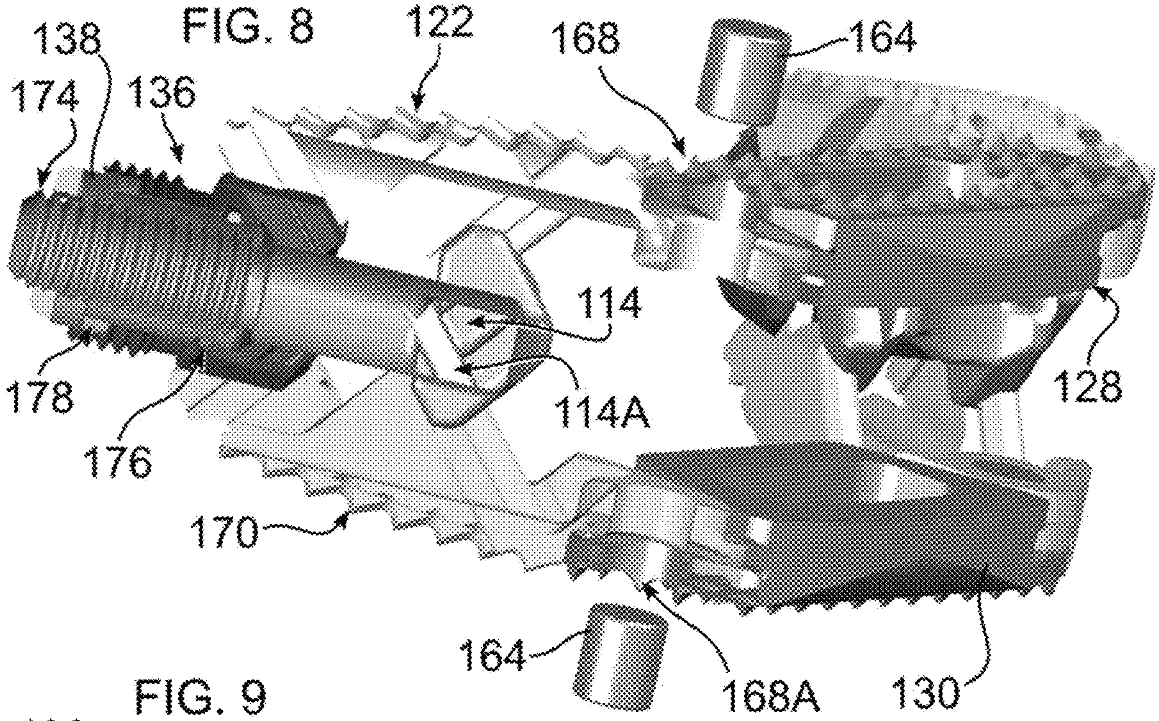
FIG. 8 is a cross-section of the device of FIG. 7, taken through a midline of one of the driven modules.
Figure 9:
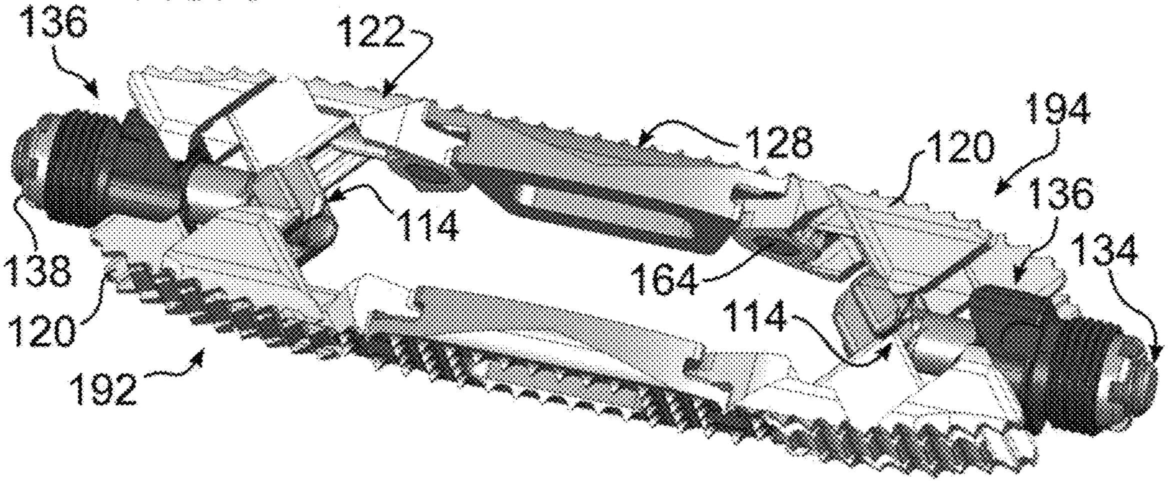
FIG. 9 is an expanded configuration of the linearly arranged device of FIG. 3.

In an embodiment, device 100 can be implanted as follows:

1. A determination is made on final optimal implant location to optimize bone mineral density of the contacted bone/implant interface.
2. Robotic/navigation is used to determine the potential trajectories that will allow for this optimal implant location to be achieved.
3. A cannula is docked on the disc space through Kambin's triangle, or the anatomical area that is bordered by the disc space, exiting nerve root, and traversing nerve root.
4. The expandable interbody is inserted in the non-articulated orientation, which can be seen in FIGS. 3 and 9;
5. The expandable interbody is fully articulated into the articulated orientation that fully maximizes surface contact area with the anterior apophyseal ring of the vertebral body (FIG. 1).
6. The expandable interbody is expanded to precisely restore normal spinal alignment (FIGS. 6-8).

During implantation, an additional portal may be used on the contralateral side of the disc space to provide an additional window through which to attach driver instrumentation to the implant and drive expansion. Articulation and expansion are achieved via threaded engagement on collar 136, for example via engagement with external threads 186, to external instrumentation. Precise placement may be achieved via navigated external drivers that allow for external visualization of the implant in three-dimensional space.

Modules 192, 194 are independently expanded via such external instrumentation that attaches to the spacer via drive features on the drive nut 138. In the embodiment shown, the nut 138 has castle teeth engagement features that allow torque transfer from an external driver. Collar 136 has external threads that allow the external driver instrumentation to rigidly connect to the implant.

In the embodiment shown, there are two driven modules 192, 194, which are joined by two link plates 128, 130. The articulation of interbody device 100 can be accomplished through different methods. In the embodiment shown in the figures, a hinge is formed by passing pin 164 through bore 166 of endplate 120 and bore 168 of link plate 128. In the embodiment shown, pin 164 passes without interference through one of endplate 120 and link plate 128, and forms an interference fit with the other of endplate 120 and link plate 128. In an alternative embodiment, pin 164 is threaded or adhered to only one of endplate 120 and link plate 128, enabling the other to move with respect to pin 164. A similar hinge is formed by pin 164A and bore 166A of endplate 122 and bore 168A of link plate 130 (FIG. 8). Alternatively, other hinge types can be used, such as a living hinge or piano hinge, as non-limiting examples. Driven module 192 is identical, or a mirror image, of driven module 194. Accordingly, herein, components of driven module 192 are given the same reference numbers as driven module 194, and are not detailed separately. Likewise, link plates 128, 130 have bilateral symmetry, and connect to each of driven modules 192, 194 in a like manner. While two link plates 128, 130 are depicted in the drawings, it should be understood that a single link plate 128 or 130 can be used.

With further reference to the drawings, and FIGS. 2, 5, and 8 in particular, device 100 is expanded using a slide system which causes the separation of endplates 120 and 122, which are each positioned within the body to contact a separate side of a bone joint relative to the other endplate. When positioned within the spine, one endplate will be a superior endplate contacting a more superior vertebra, and the other endplate will be an inferior endplate, contacting a more inferior vertebra. An orientation of device 100 may be determined by the side of the body from which implantation is approached.

In particular, and with reference to FIG. 2, driven module 192 (or 194) includes endplates 120, 122 which each have a bone engaging exterior side, which can include projections 170 for engaging bone, and an opposed interior side having first and second parallel ramp pairs 110, 112 for endplate 120, and ramp pairs 110A, 112A for endplate 122. The ramps of the first pair are angled in an opposite direction with respect to the angle of the ramps of the second pair.

A threaded shaft 134 includes two pairs of ramp followers 114, 114A, which are positioned at a distal end 180 of shaft 134 to engage and slide along ramp pairs 112 and 112A. A collar 136 includes a smooth bore 174 sized to rotatably support a nut 138, in this embodiment a castle nut, which is threaded onto a proximal threaded portion 176 of shaft 134. Collar 136 is rotatably engaged with nut 138 by a snap ring 176. As can best be seen in FIG. 9, snap ring 176 is positioned between an end of the threaded portion 174 and an internal channel 178 formed within collar bore 174. As a result, nut 138 can rotate within collar bore 174, but is not displaced axially along collar bore 174. A bushing 178 reduces friction between nut 138 and collar 136 as nut 138 is rotated.

Collar 136 includes ramp follower pairs 116, 116A, which engage with and follow ramp pairs 110, 110A. Thus, as nut 138 is rotated upon shaft threaded portion 174, nut 138 advances axially along shaft 134. Collar 136, being keyed to nut 138 via snap ring 176, advances together with nut 138, but as bore 174 is smooth, collar 136 does not rotate radially about shaft 134. As nut 138 advances axially along shaft 134, a distance between collar 136 and shaft distal end 180 is reduced. As a result, ramp follower pairs 114, 114A and collar ramp follower pairs 116, 116A are driven along ramp pairs 110, 110A and 112, 112A, which forces endplates 120, 122 away from each other.

In the embodiment shown, the angle of ramps 110, 110A and 112, 112A mutually correspond to cause endplates 120, 122 to remain parallel with respect to each other as device 100 expands with the separation of endplates 120, 122. In an alternative embodiment, ramp pairs 110, 110A can have a different angle than ramp pairs 112, 112A, which would result in a non-planar orientation of endplates 120, 122, which can be used to address lordosis or other angular relationship of bones of a joint.

As shown by arrows “A” and “B” in FIG. 5A, ramp followers 114, 114A, 116, and 116A form a dovetail type connection with ramp pairs 110, 110A, 112, 112A, for greater stability and reliability, although other mating and sliding engagements can be used. Additionally, while ramp pairs 110, 110A, 112, 112A are provided as pairs for secure lateral stability, it should be understood that these ramps can be provided as single ramps, wherein stability is obtained solely through the dovetail connection formed with a respective ramp follower 114, 114A, 116, 116A. For example, the connection could be wider or otherwise include additional overlap to provide sufficient stability, and could have an alternative shape, such as mating L-shapes.

As endplates 120, 122 separate, they cause a separation of link plates 128, 130, respectively, via connections with pins 164. Driven modules 192 and 194 can be driven separately, so that one end of link plates 128, 130 can separate at a different rate and to a different extent from an opposite end of link plates 128, 130. If driven modules are expanded to different extents, particular bone geometry, such as lordosis or scoliosis, can be specifically addressed.

Pin 164 can have an alternative shape, such as is shown for pin 164A in FIG. 2A, which includes a cylinder portion 196 which is attached to a spheroidal, oval, or other curved shape portion 198. The curved shape portion 198 is positioned within a portion of endplate 122 or 120, or alternatively link plate 128 or 130, which has a mating internal curved socket (not shown). The cylindrical portion 196 is affixed to one of an endplate or a link plate, for example by a press fit, interference fit, adhesive, or other fastening method, and the curved portion remains movable with respect to the socket of the other of the endplate or link plate. This enables an endplate to hingedly connect to a link plate and for these hinged elements to be movable with respect to each other along more than one axis.

To enable the smallest possible implantation profile of device 100, ramp pairs 110, 110A are offset with respect to ramp pairs 112, 112A. Gaps 182 and openings 184 are formed in endplates 120, 122, which together with the aforementioned offset, enable complete nesting and overlap of endplates 120, 122 and ramps 110, 110A, 112, 112A, as can be seen for example in FIG. 3. Gaps 182 and openings 184 are opened when device 100 is expanded, thereby providing routes for bony ingrowth through device 100. Bony ingrowth can additional take place through openings 190 in link plates 128, 130.

Collar 136 is provided with an external thread 186, which can be threadably engaged by an installation tool, for example a cannula with a threaded and rotatable end. Guide grooves 188 are additionally provided to facilitate manipulation of device 100.

Advantages of device 100 include, at least:

1. A small insertion profile: the disclosure enables, for example, an 8.5 mm insertion profile into the disc space, reducing the required skin, fascia, muscle, and ligamentous disruption. Smaller profiles can be achieved, including profiles as small as 6 mm, for example, or profiles substantially larger than 8.5 mm.
2. Controlled lordosis: the disclosure enables controlled lordosis through placement of device 100 in an articulated position in the disc space. The device 100 can be configured with a specific amount of lordosis that can be realized as it is expanded within the disc space. The broad footprint of the device provides a strong and stable platform to establish and maintain lordosis correction.
3. Reduced endplate disruption: due to the ability of device 100 to expand a correct, therapeutic extent in situ, the disclosure reduces the need for traditional trialing through the insertion of interbody implants of various sizes, the latter potentially causing or contributing to vertebral endplate disruption and further trauma to the body.
4. Increased implant surface area in a smaller insertion profile on optimal bone: Due to the articulation mechanism, additional implant-bone contact surface area can be achieved through a small access window. Additionally, implant placement on harder cortical bone along the anterior apophyseal may be achieved.
5. Coronal correction can also be achieved by the fact that each side of the implant can be adjusted independently. This enables the medical practitioner to utilize the implant to even out asymmetric vertebrae and address coronal deformity as needed.

With reference to FIG. 10, a driving tool 400 forms a cannula. Indicia 402 indicates an insertion depth of tool 400 into the body. Positioning is carried out using imaging, and can further be carried out using a robotics system. The bore 404 of tool 400 enables the insertion of surgical instruments in order to cut, excise, or cauterize body tissue, and to otherwise facilitate a surgical procedure to implant device 100. Bore 404 is further sized to enable passage of device 100. To minimize the required size of bore 404, device 100 is configured in the smallest height profile, and is articulated to a straightened configuration, as shown in FIG. 1, to be inserted into the body through bore 404. A second tool 400 can be employed, whereby an ipsilateral and contralateral tool pair facilitates positioning and articulation (height expansion and contraction by rotating nut 138). After device 100 exits tool 400 within the body, it may be manipulated into a position upon the vertebral endplate 300, for example upon the apophyseal ring 302, using surgical tools passed through tool 400. At a later date, if needed, tool 400 can be reinserted into the body to change reposition device 100, change a height of device 100 by rotating nut 138, and/or device 100 can be removed from the body if therapeutically beneficial.

Different devices 100 may include ramps 110, 110A, 112, 112A of differing angle, height, or length relative to other devices 100, to enable expansion at different rates or extents, as indicated for therapeutic treatment. Fewer or a greater number of ramps and/or ramp followers can be provided. Endplates 120, 122 may additionally, or alternatively, be resilient, so that they may conform to bony surfaces, forming a more stable support platform. Accordingly, endplates 120, 122 can be fabricated from a polymeric material, a naturally resilient material, or a resilient metal, for example a shape memory alloy, or any other resilient biocompatible material of sufficient strength and durability for separating bones within the body.

Device 100D can be inserted at a contracted height transforaminally, for example, and are capable of articulating into anterior placement. Once placement is achieved, device 100 is capable of expanding for disc height restoration. Additionally, device 100 can be positioned anteriorly, and can be expanded through a continuous range to provide axial balance and greater endplate contact area. Additionally, device 100 enables superior sagittal correction, through the use of a relatively smaller insertion window, decreasing the need for bone damage. Thus, device 100 provides the benefits of an ALIF device through a familiar posterior approach, decreasing surgery time and associated blood loss, as well as eliminating the need for an access surgeon.

In accordance with the disclosure, during implantation of intervertebral spacers from a posterior approach, there is a need to avoid damaging nerve roots. A prior art spacer dimensioned to separate bones can block a view of nerve roots as it is inserted, and due to its large size, poses a greater risk of contacting nerve roots during insertion into the body. As a result, the medical practitioner must more often retract nerve roots, with attendant danger of tissue damage. Devices 100 of the disclosure form a smaller dimension during implantation, relative to a final dimension for spacing bones. Accordingly, nerve roots can be visualized and avoided during insertion, and nerve root manipulation can be avoided or minimized.

As devices 100 of the disclosure can be articulated during implantation, they can be inserted between bones by being passed through a minimally invasive entry, for example through an incision approximating the smallest collapsed dimension, for example transverse to the longitudinal dimension. This enables exceptional anterior placement without impaction, as well as facilitating implantation from other approaches. Devices 100 of the disclosure further develop a good bone contact area, as an implant with a larger footprint may be inserted through a reduced size incision, due to the overall dimensions of device 100 being reduced during insertion.

Devices 100 of the disclosure enable a continuous expansion and distraction over a range of displacements according to predetermined dimensions of a specific spacer design. This provides the ability to distract vertebral bodies or other bones to a desired height or separation. Endplates 120, 122 can be shaped to form planes or surfaces which converge relative to each, to provide for proper lordosis, and can be provided with gaps 182 and openings 184 through which bone may grow, and into which bone graft material may be placed. Devices 100 of the disclosure may be used to distract, or force bones of a joint apart, or may be used to maintain a separation of bones created by other means, for example by a retractor. Endplates may additionally be curved to conform to the surface of body tissue, for example the surface of cortical bone, of the vertebra to be contacted, for improved fixation and load bearing.

Devices 100 of the disclosure may be further secured in connection with the body by passage of elongated fasteners through an endplate 120, 122. A blocking mechanism can be used to prevent backing out of an elongated fastener.

Devices 100 of the disclosure may be fabricated using any biocompatible materials known or hereinafter discovered, having sufficient strength, flexibility, resiliency, and durability for the patient, and for the term during which the device is to be implanted. Examples include but are not limited to metal, such as, for example titanium and chromium alloys; polymers, including for example, PEEK or ultra high molecular weight polyethylene (UHMWPE); and ceramics. There are many other biocompatible materials which may be used, including other plastics and metals, as well as fabrication using living or preserved tissue, including autograft, allograft, and xenograft material.

Portions or all of device 100 may be radiopaque or radiolucent, or materials having such properties may be added or incorporated into device 100 to improve imaging of the device during and after implantation.

Devices 100 may be formed using titanium, or a cobalt-chrome-molybdenum alloy, Co—Cr—Mo, for example as specified in ASTM F1537 (and ISO 5832-12). The smooth surfaces may be plasma sprayed with commercially pure titanium, as specified in ASTM F1580, F1978, F1147 and C-633 (and ISO 5832-2). Alternatively, part or all of devices 100 may be formed with a polymer, for example ultra-high molecular weight polyethylene, UHMWPE, for example as specified in ASTM F648 (and ISO 5834-2). In one embodiment, PEEK-OPTIMA (a trademark of Invibio Ltd Corp, United Kingdom) may be used for one or more components of devices 100 of the disclosure. For example, polymeric portions can be formed with PEEK-OPTIMA, which is radiolucent, whereby bony ingrowth may be observed. Other polymeric materials with suitable flexibility, durability, and biocompatibility may also be used.

In accordance with the invention, implants of various sizes may be provided to best fit the anatomy of the patient. Components of matching or divergent sizes may be assembled during the implantation procedure by a medical practitioner as best meets the therapeutic needs of the patient, the assembly inserted within the body using an insertion tool. Devices 100 of the invention may also be provided with an overall angular geometry, for example an angular mating disposition of endplates, to provide for a natural lordosis, or a corrective lordosis, for example of from 0° to 22° for a cervical, thoracic or lumbar application, although much different values may be advantageous for other joints. Lordotic angles may also be formed by shaping one or both endplates to have relatively non-coplanar surfaces.

Expanded implant heights, for use in the lumbar vertebrae for example, may typically range from 7 mm to 17 mm, but may be larger or smaller, including as small as 5 mm, and as large as 21 mm, although the size is dependent on the patient, and the joint into which an implant of the invention is to be implanted. Devices 100 may be implanted within any level of the spine, and may also be implanted in other joints of the body, including joints of the hand, wrist, elbow, shoulder, hip, knee, ankle, or foot.

In accordance with the invention, a single device 100 may be used, to provide stabilization for a weakened joint or joint portion. Alternatively, a combination of two, three, or more of any of device 100 may be used in multiple joints. Moreover, implants of the disclosure may be combined with other stabilizing means.

Additionally, devices 100 of the disclosure may be fabricated using material that biodegrades in the body during a therapeutically advantageous time interval, for example after sufficient bone ingrowth has taken place. Further, implants of the disclosure are advantageously provided with smooth and or rounded exterior surfaces, which reduce a potential for deleterious mechanical effects on neighboring tissues.

Any surface or component of a device 100 of the disclosure may be coated with or impregnated with therapeutic agents, including bone growth, healing, antimicrobial, or drug materials, which may be released at a therapeutic rate, using methods known to those skilled in the art.

Devices of the disclosure provide for adjacent vertebrae to be supported during flexion/extension, lateral bending, and axial rotation. In one embodiment, device 100 is indicated for spinal arthroplasty in treating skeletally mature patients with degenerative disc disease, primary or recurrent disc herniation, spinal stenosis, or spondylosis in the lumbosacral spine (LI-SI). Degenerative disc disease is advantageously defined as discogenic back pain with degeneration of the disc confirmed by patient history and radiographic studies, with or without leg (radicular) pain. Patients are advantageously treated, for example, who may have spondylolisthesis up to Grade 1 at the involved level. The surgery position device 100 may be performed through an Anterior, Anterolateral, Posterolateral, Lateral, or any other approach.

In a typical embodiment, devices 100 of the disclosure have an uncompressed height, before insertion, of 6 to 13 mm, and may advantageously be provided in cross-sections of 8×45, 8×50, 8×55, 8×60, 10×50 mm, 12×60 mm and 12×65 mm, with 4, 8, 12, 15, 20, 25, or 30 degree lordotic angles, although these are only representative sizes, and substantially smaller or larger sizes can be therapeutically beneficial. In one embodiment implants in accordance with the instant disclosure are sized to be inserted using an MIS approach, for example using a reduced incision size, for example less than about 5 cm, and advantageously less than about 1 cm, with fewer and shorter cuts through body tissue. Device 100 may advantageously be used in combination with other known or hereinafter developed forms of stabilization or fixation, including for example rods and plates, or intradiscal fixation, potentially connecting device 100 to one or more of the adjacent vertebrae.

All references cited herein are expressly incorporated by reference in their entirety. It will be appreciated by persons skilled in the art that the present disclosure is not limited to what has been particularly shown and described herein above. In addition, unless mention was made above to the contrary, it should be noted that all of the accompanying drawings are not to scale. There are many different features to the present disclosure and it is contemplated that these features may be used together or separately. Thus, the disclosure should not be limited to any particular combination of features or to a particular application of the disclosure. Further, it should be understood that variations and modifications within the spirit and scope of the disclosure might occur to those skilled in the art to which the disclosure pertains. Accordingly, all expedient modifications readily attainable by one versed in the art from the disclosure set forth herein that are within the scope and spirit of the present disclosure are to be included as further embodiments of the present disclosure.

| Drawing References: |
|---|
| 100 device |
| 110, 110A, 112, 112A ramp pair |
| 114, 114A shaft ramp follower pair |
| 116, 116A collar ramp follower pair |
| 120, 122 endplate |

-continued

| Drawing References: |
|---|
| 128, 130 link plate |
| 134 threaded shaft |
| 136 collar |
| 138 nut |
| 150, 152 dovetail surface |
| 154 proximal end |
| 156, 156A cutout portion |
| 158 relief |
| 160 vertical surface |
| 162 sleeve |
| 164, 164A pin |
| 166, 166A, 168, 168A bore |
| 170 projection |
| 174 collar bore |
| 174 shaft threaded portion |
| 176 snap ring |
| 178 bushing |
| 180 shaft distal end |
| 182 endplate gap |
| 184 endplate opening |
| 186 collar external threads |
| 188 collar guide grooves |
| 190 link plate opening |
| 192, 194 driven modules |
| 196 cylindrical pin portion |
| 198 curved pin portion |
| 300 vertebral endplate |
| 302 apophyseal ring |
| 400 driving tool |
| 402 indicia |
| 404 tool bore |

What is claimed is:

1. A method for stabilizing adjacent vertebral bodies, said method comprising:

providing a spacer for separating bones of a joint;

inserting the spacer between the adjacent vertebral bodies; and positioning the spacer into a deployment position, wherein the spacer includes:

first and second driven modules, each including:

first and second endplates, each having a first side forming a bone engaging surface, and a second side opposite to the first side and having at least two ramps extending from the second side in a direction away from the first side;

a shaft having a first end having threads, and a second end opposite to the first end having at least two ramp followers each mateable with a ramp of the second side of one of the first and second endplates;

a collar slidably disposed upon the shaft proximate the shaft first end, the collar having at least two ramp followers each mateable with a ramp of the second side of one of the first and second endplates;

a nut threadably engaged with the shaft first end, the nut rotatable to push the collar in the direction of the shaft second end to thereby slide the at least two ramp followers of the second end of the shaft and the at least two ramp followers of the collar against mated ramps of the first and second endplates to thereby push the endplates apart relative to each other; and a pair of link plates each having first and second spaced apart opposed ends pivotally joined to one of the first and second endplates of the first and second driven modules by a hinge connection, each link plate having a bone engaging surface such that when the first and second driven modules are vertically expanded, the link plates also expand vertically in the same direction such that the bone engaging surfaces of the link plates push against the bones to separate the bones of the joint, wherein in the collapsed position a first angled side of the first endplate engages a first angled side of the second endplate and in the expanded position the first angled side of the first endplate is separated from the first angled side of the second endplate.

2. The method of claim 1, wherein the endplates are driven relatively apart by rotating the nut when the spacer is in the deployment position.

3. The method of claim 1, each one of the pair of link plates having first and second spaced apart opposed ends, a hinge including a pin connecting a driven module at each of the first and second ends.

4. The method of claim 1, one of the pair of link plates is hingedly connected to two first endplates, the other one of the pair of link plates is hingedly connected to two second endplates, the pair of link plates are separated from each other when the first and second endplates are pushed apart.

5. The method of claim 1, the first and second modules and one of the pair of link plates are alignable relative to each other to form a linear spacer, the linear spacer thereby being insertable through a cannula into a body.

6. The method of claim 1, the first and second modules each pivotable about the hinge connection to form the spacer into a U-shaped configuration, the U-shaped configuration formable when the spacer is between two bony surfaces.

7. The method of claim 1, the hinge connection including a pin affixed to one of an endplate and one of the link plates, the pin movably connected to the other of the endplate and one of the link plates.

8. The method of claim 7, the pin forming a curved surface where the pin is movably connected.

9. The method of claim 1, the collar of each of the two driven modules including an external threaded sleeve engageable by a surgical tool to couple the spacer and the tool.

10. The method of claim 1, the at least two ramp followers of the collar each including a dovetail portion mateable with a ramp of an endplate second side.

11. A method for stabilizing adjacent vertebral bodies, said method comprising:

providing a spacer for separating bones of a joint;

inserting the spacer between the adjacent vertebral bodies; and positioning the spacer into a deployment position, wherein the spacer includes:

first and second driven modules, each including:

first and second endplates, each having a first side forming a bone engaging surface, and a second side opposite to the first side and having at least two spaced apart pairs of ramps extending from the second side in a direction away from the first side;

a shaft having a first end having threads, and a second end opposite to the first end having at least two spaced apart pairs of ramp followers each mateable with a pair of ramps of the second side of one of the first and second endplates;

a collar slidably disposed upon the shaft proximate the shaft first end, the collar having at least two pairs of ramp followers each mateable with a pair of ramps of the second side of one of the first and second endplates;

whereby the pairs of ramps of the first and second endplates face each other, and the bone engaging surfaces of the first and second endplates face in opposite directions relative to each other, when the pairs of ramps of the first and second endplates are mated with the ramp followers of the shaft second end and the collar; and a nut threadably engaged with the shaft first end, the nut rotatable to push the collar in the direction of the shaft second end to thereby slide the at least two pairs of ramp followers of the second end of the shaft and the at least two pairs of ramp followers of the collar against mated ramp pairs of the first and second endplates to thereby push the endplates apart relative to each other; and a pair of link plates each having first and second spaced apart opposed ends pivotally joined to one of the first and second endplates of the first and second driven modules by a hinge connection, each link plate having a bone engaging surface such that when the first and second driven modules are vertically expanded, the link plates also expand vertically in the same direction such that the bone engaging surfaces of the link plates push against the bones to separate the bones of the joint, wherein in the collapsed position a first angled side of the first endplate engages a first angled side of the second endplate and in the expanded position the first angled side of the first endplate is separated from the first angled side of the second endplate.

* * * * *